(12) United States Patent
Haslinger et al.

(10) Patent No.: US 9,381,325 B2
(45) Date of Patent: *Jul. 5, 2016

(54) ROBUST CATHETER TUBING

(71) Applicant: Abbott Cardiovascular Systems, Inc., Santa Clara, CA (US)

(72) Inventors: Thomas Haslinger, Sun City, CA (US); Jeong S. Lee, Diamond Bar, CA (US); Neftali Fernandez, Moreno Valley, CA (US); John A. Simpson, Carlsbad, CA (US)

(73) Assignee: ABBOTT CADIOVASCULAR SYSTEMS, INC., Santa Clara, CA (US)

( * ) Notice: Subject to any disclaimer, the term of this patent is extended or adjusted under 35 U.S.C. 154(b) by 656 days.

This patent is subject to a terminal disclaimer.

(21) Appl. No.: 13/898,027

(22) Filed: May 20, 2013

(65) Prior Publication Data

US 2013/0253425 A1   Sep. 26, 2013

Related U.S. Application Data

(63) Continuation of application No. 12/478,929, filed on Jun. 5, 2009, now Pat. No. 8,444,608, which is a continuation-in-part of application No. 12/324,425, filed on Nov. 26, 2008, now Pat. No. 8,070,719.

(51) Int. Cl.
*A61M 5/00* (2006.01)
*A61M 25/00* (2006.01)
(Continued)

(52) U.S. Cl.
CPC .............. *A61M 25/10* (2013.01); *A61L 29/041* (2013.01); *A61L 29/06* (2013.01); *A61L 29/085* (2013.01); *A61M 25/005* (2013.01);
(Continued)

(58) Field of Classification Search
CPC . Y10T 29/494; Y10T 29/49401; Y10T 29/54; B32B 2535/00; A61M 25/10; A61L 29/06
USPC .......................................... 604/96.01–103.14
See application file for complete search history.

(56) References Cited

U.S. PATENT DOCUMENTS

| 4,425,919 A | 1/1984 | Alston et al. |
|---|---|---|
| 4,563,181 A | 1/1986 | Wijayarathna et al. |

(Continued)

FOREIGN PATENT DOCUMENTS

| EP | 0 277 368 | 8/1988 |
|---|---|---|
| EP | 0 414 350 | 2/1991 |

(Continued)

OTHER PUBLICATIONS

U.S. Appl. No. 14/950,414, Nov. 24, 2015.

(Continued)

*Primary Examiner* — Jason L Vaughan
*Assistant Examiner* — Amanda Meneghini
(74) *Attorney, Agent, or Firm* — Baker Botts L.L.P.

(57) ABSTRACT

A balloon catheter having a multilayer catheter shaft is formed to have an inner layer and an outer layer, where the inner layer and outer layer are selected from materials that enhance the pushability of the catheter while preserving the flexibility. Using a combination of a high Shore D duromater value material and a lower Shore D duromater value material, various combinations of multilayer catheter shafts are disclosed utilizing different glass transition temperatures and block copolyamides to obtain the desired characteristics.

30 Claims, 3 Drawing Sheets

(51) Int. Cl.
*A61M 29/00* (2006.01)
*A61M 25/10* (2013.01)
*A61L 29/04* (2006.01)
*A61L 29/06* (2006.01)
*A61L 29/08* (2006.01)

(52) U.S. Cl.
CPC ........ *A61M 25/0045* (2013.01); *A61M 25/104* (2013.01); *A61M 25/1006* (2013.01); *A61M 25/0009* (2013.01); *A61M 2025/1061* (2013.01)

(56) References Cited

U.S. PATENT DOCUMENTS

| | | |
|---|---|---|
| 4,596,563 A | 6/1986 | Pande |
| 4,775,371 A | 10/1988 | Mueller, Jr. |
| 4,820,349 A | 4/1989 | Saab |
| 4,877,031 A | 10/1989 | Conway et al. |
| 4,886,506 A | 12/1989 | Lovgren et al. |
| 4,892,519 A | 1/1990 | Songer et al. |
| 4,952,357 A | 8/1990 | Euteneuer |
| 4,955,895 A | 9/1990 | Sugiyama et al. |
| 4,960,410 A | 10/1990 | Pinchuk |
| 4,976,720 A | 12/1990 | Machold et al. |
| 4,994,047 A | 2/1991 | Walker et al. |
| 5,047,045 A | 9/1991 | Arney et al. |
| 5,061,273 A | 10/1991 | Yock |
| 5,078,702 A | 1/1992 | Pomeranz |
| 5,085,649 A | 2/1992 | Flynn et al. |
| 5,112,304 A | 5/1992 | Barlow et al. |
| 5,156,594 A | 10/1992 | Keith |
| 5,176,661 A | 1/1993 | Evard et al. |
| 5,195,969 A | 3/1993 | Wang et al. |
| 5,205,822 A | 4/1993 | Johnson et al. |
| 5,207,700 A | 5/1993 | Euteneuer |
| 5,217,434 A | 6/1993 | Arney |
| 5,217,482 A | 6/1993 | Keith |
| 5,250,059 A | 10/1993 | Andreas et al. |
| 5,270,086 A | 12/1993 | Hamlin |
| 5,277,199 A | 1/1994 | DuBois et al. |
| 5,290,232 A | 3/1994 | Johnson et al. |
| 5,290,306 A | 3/1994 | Trotta et al. |
| 5,300,025 A | 4/1994 | Wantink |
| 5,304,134 A | 4/1994 | Kraus et al. |
| 5,312,430 A | 5/1994 | Rosenbluth et al. |
| 5,318,032 A | 6/1994 | Lonsbury et al. |
| 5,318,526 A | 6/1994 | Cohen |
| 5,334,146 A | 8/1994 | Ozasa |
| 5,342,386 A | 8/1994 | Trotta |
| 5,358,486 A | 10/1994 | Saab |
| 5,364,357 A | 11/1994 | Aase |
| 5,370,616 A | 12/1994 | Keith et al. |
| 5,378,238 A | 1/1995 | Peters et al. |
| 5,395,336 A | 3/1995 | Barclay et al. |
| 5,425,712 A | 6/1995 | Goodin |
| 5,447,497 A | 9/1995 | Sogard et al. |
| 5,451,233 A | 9/1995 | Yock |
| 5,454,789 A | 10/1995 | Burns et al. |
| 5,470,315 A | 11/1995 | Adams |
| 5,476,477 A | 12/1995 | Burns |
| 5,478,320 A | 12/1995 | Trotta |
| 5,484,409 A | 1/1996 | Atkinson et al. |
| 5,490,837 A | 2/1996 | Blaeser et al. |
| 5,496,275 A | 3/1996 | Sirhan et al. |
| 5,499,980 A | 3/1996 | Euteneuer |
| 5,507,766 A | 4/1996 | Kugo et al. |
| 5,512,051 A | 4/1996 | Wang et al. |
| 5,526,823 A | 6/1996 | Wheeler |
| 5,538,510 A | 7/1996 | Fontirroche et al. |
| 5,538,513 A | 7/1996 | Okajima |
| 5,545,134 A | 8/1996 | Hilaire et al. |
| 5,549,552 A | 8/1996 | Peters et al. |
| 5,554,121 A | 9/1996 | Ainsworth et al. |
| 5,556,383 A | 9/1996 | Wang et al. |
| 5,569,195 A | 10/1996 | Saab |
| 5,587,125 A | 12/1996 | Roychowdhury |
| 5,599,326 A | 2/1997 | Carter |
| 5,613,979 A | 3/1997 | Trotta et al. |
| 5,620,649 A | 4/1997 | Trotta |
| 5,622,665 A | 4/1997 | Wang |
| 5,632,760 A | 5/1997 | Sheiban et al. |
| 5,643,209 A | 7/1997 | Fugoso et al. |
| 5,658,264 A | 8/1997 | Samson |
| 5,690,613 A | 11/1997 | Verbeek |
| 5,728,063 A | 3/1998 | Preissman et al. |
| 5,743,874 A | 4/1998 | Fischell et al. |
| 5,743,875 A | 4/1998 | Sirhan et al. |
| 5,749,849 A | 5/1998 | Engelson et al. |
| 5,755,690 A | 5/1998 | Saab |
| 5,759,173 A | 6/1998 | Preissman et al. |
| 5,766,151 A | 6/1998 | Valley et al. |
| 5,769,817 A | 6/1998 | Burgmeier |
| 5,769,819 A | 6/1998 | Schwab et al. |
| 5,775,327 A | 7/1998 | Randolph et al. |
| 5,779,731 A | 7/1998 | Leavitt |
| 5,782,811 A | 7/1998 | Samson et al. |
| 5,791,036 A | 8/1998 | Goodin et al. |
| 5,792,124 A | 8/1998 | Horrigan et al. |
| 5,792,144 A | 8/1998 | Fischell et al. |
| 5,795,325 A | 8/1998 | Valley et al. |
| 5,795,341 A | 8/1998 | Samson |
| 5,797,887 A | 8/1998 | Rosen et al. |
| 5,814,016 A | 9/1998 | Valley et al. |
| 5,820,594 A | 10/1998 | Fontirroche et al. |
| 5,833,657 A | 11/1998 | Reinhardt et al. |
| 5,853,400 A | 12/1998 | Samson |
| 5,879,369 A | 3/1999 | Ishida |
| 5,879,499 A | 3/1999 | Corvi |
| 5,902,290 A | 5/1999 | Peacock et al. |
| 5,908,406 A | 6/1999 | Ostapchenko et al. |
| 5,911,715 A | 6/1999 | Berg et al. |
| 5,916,193 A | 6/1999 | Stevens et al. |
| 5,947,939 A | 9/1999 | Mortier et al. |
| 5,964,778 A | 10/1999 | Fugoso et al. |
| 5,989,218 A | 11/1999 | Wasicek |
| 6,004,289 A | 12/1999 | Saab |
| 6,004,339 A | 12/1999 | Wijay |
| 6,010,521 A | 1/2000 | Lee et al. |
| 6,021,340 A | 2/2000 | Randolph et al. |
| 6,024,693 A | 2/2000 | Schock et al. |
| 6,024,722 A | 2/2000 | Rau et al. |
| 6,027,510 A | 2/2000 | Alt |
| 6,036,670 A | 3/2000 | Wijeratne et al. |
| 6,056,719 A | 5/2000 | Mickley |
| 6,059,751 A | 5/2000 | Ostapchenko et al. |
| 6,059,770 A | 5/2000 | Peacock et al. |
| 6,071,266 A | 6/2000 | Kelley |
| 6,086,556 A | 7/2000 | Hamilton et al. |
| 6,102,890 A | 8/2000 | Stivland et al. |
| 6,124,007 A | 9/2000 | Wang et al. |
| 6,132,824 A | 10/2000 | Hamlin |
| 6,136,258 A | 10/2000 | Wang et al. |
| 6,146,356 A | 11/2000 | Wang et al. |
| 6,165,166 A | 12/2000 | Samuelson et al. |
| 6,165,195 A | 12/2000 | Wilson et al. |
| 6,168,588 B1 | 1/2001 | Wilson |
| 6,171,275 B1 | 1/2001 | Webster, Jr. et al. |
| 6,171,278 B1 | 1/2001 | Wang et al. |
| 6,179,810 B1 | 1/2001 | Wantik et al. |
| 6,179,856 B1 | 1/2001 | Barbere |
| 6,193,686 B1 | 2/2001 | Estrada et al. |
| 6,197,015 B1 | 3/2001 | Wilson |
| 6,210,396 B1 | 4/2001 | MacDonald et al. |
| 6,217,547 B1 | 4/2001 | Lee |
| 6,217,565 B1 | 4/2001 | Cohen |
| 6,242,063 B1 | 6/2001 | Ferrera et al. |
| 6,245,053 B1 | 6/2001 | Benjamin |
| 6,251,093 B1 | 6/2001 | Valley et al. |
| 6,264,683 B1 | 7/2001 | Stack et al. |
| 6,265,016 B1 | 7/2001 | Hostettler et al. |
| 6,306,097 B1 | 10/2001 | Park et al. |
| 6,306,124 B1 | 10/2001 | Jones et al. |
| 6,308,342 B1 | 10/2001 | Qi et al. |
| 6,358,227 B1 | 3/2002 | Ferrera et al. |
| 6,364,894 B1 | 4/2002 | Healy et al. |

(56) References Cited

U.S. PATENT DOCUMENTS

| | | |
|---|---|---|
| 6,402,720 B1 | 6/2002 | Miller et al. |
| 6,416,494 B1 | 7/2002 | Wilkins |
| 6,482,348 B1 | 11/2002 | Wang |
| 6,495,090 B1 | 12/2002 | Wilkins et al. |
| 6,495,127 B1 | 12/2002 | Wallace et al. |
| 6,500,148 B1 | 12/2002 | Pinchuk et al. |
| 6,508,784 B1 | 1/2003 | Shu |
| 6,530,938 B1 | 3/2003 | Lee et al. |
| 6,548,010 B1 | 4/2003 | Stivland et al. |
| 6,575,934 B2 | 6/2003 | Duchamp |
| 6,575,958 B1 | 6/2003 | Happ et al. |
| 6,579,259 B2 | 6/2003 | Stevens et al. |
| 6,585,687 B1 | 7/2003 | Shkolnik |
| 6,585,688 B2 | 7/2003 | Ferrera et al. |
| 6,589,207 B1 | 7/2003 | El-Nounou |
| 6,589,226 B1 | 7/2003 | Owens |
| 6,591,472 B1 | 7/2003 | Noone et al. |
| 6,620,127 B2 | 9/2003 | Lee et al. |
| 6,620,128 B1 | 9/2003 | Simhambhatla |
| 6,626,889 B1 | 9/2003 | Simpson et al. |
| 6,629,961 B1 | 10/2003 | Israelsson et al. |
| 6,645,422 B2 | 11/2003 | Jung, Jr. et al. |
| 6,648,854 B1 | 11/2003 | Patterson et al. |
| 6,663,614 B1 | 12/2003 | Carter et al. |
| 6,673,291 B1 | 1/2004 | Field et al. |
| 6,673,302 B2 | 1/2004 | Wang et al. |
| 6,695,809 B1 | 2/2004 | Lee |
| 6,702,802 B1 | 3/2004 | Hancock et al. |
| 6,718,211 B2 | 4/2004 | Smits et al. |
| 6,733,487 B2 | 5/2004 | Keith et al. |
| 6,756,094 B1 | 6/2004 | Wang et al. |
| 6,777,644 B2 | 8/2004 | Peacock et al. |
| 6,793,647 B1 | 9/2004 | Cryer |
| 6,796,958 B2 | 9/2004 | Chen et al. |
| 6,796,960 B2 | 9/2004 | Cioanta et al. |
| 6,835,189 B2 | 12/2004 | Musbach et al. |
| 6,837,890 B1 | 1/2005 | Chiudzinski |
| 6,863,678 B2 | 3/2005 | Lee et al. |
| 6,875,197 B1 | 4/2005 | Simhambhatia et al. |
| 6,887,219 B2 | 5/2005 | Wantink et al. |
| 6,890,395 B2 | 5/2005 | Simhanbhatia |
| 6,893,456 B2 | 5/2005 | Lumauig |
| 6,911,038 B2 | 6/2005 | Mertens et al. |
| 6,913,600 B2 | 7/2005 | Valley et al. |
| 6,918,920 B1 | 7/2005 | Wang et al. |
| 6,946,092 B1 | 9/2005 | Bertolino et al. |
| 6,951,555 B1 | 10/2005 | Suresh |
| 6,951,675 B2 | 10/2005 | Chin et al. |
| 6,979,342 B2 | 12/2005 | Lee et al. |
| 7,026,026 B2 | 4/2006 | Ferrera et al. |
| 7,029,732 B2 | 4/2006 | Wang et al. |
| 7,037,291 B2 | 5/2006 | Lee et al. |
| 7,037,295 B2 | 5/2006 | Tiernan et al. |
| 7,074,206 B2 | 7/2006 | Lee et al. |
| 7,108,877 B2 | 9/2006 | Blair et al. |
| 7,112,357 B2 | 9/2006 | Miller et al. |
| 7,141,059 B2 | 11/2006 | Duchamp et al. |
| 7,147,817 B1 | 12/2006 | Lim et al. |
| 7,163,523 B2 | 1/2007 | Devens, Jr. et al. |
| 7,195,638 B1 | 3/2007 | Sridharan |
| 7,273,485 B2 | 9/2007 | Simpson et al. |
| 7,335,185 B2 | 2/2008 | Tang et al. |
| 7,341,571 B1 | 3/2008 | Harris et al. |
| 7,556,634 B2 | 7/2009 | Lee et al. |
| 7,662,130 B2 | 2/2010 | Lee et al. |
| 7,828,766 B2 | 11/2010 | Durcan |
| 7,833,193 B2 | 11/2010 | Lee et al. |
| 7,906,066 B2 | 3/2011 | Wilson et al. |
| 7,947,059 B2 | 5/2011 | Chin et al. |
| 8,012,300 B2 | 9/2011 | Simpson et al. |
| 8,052,638 B2 | 11/2011 | Lee et al. |
| 8,070,719 B2 | 12/2011 | Lee et al. |
| 8,382,738 B2 | 2/2013 | Simpson et al. |
| 8,388,602 B2 | 3/2013 | Simpson et al. |
| 8,403,885 B2 | 3/2013 | Arana et al. |
| 8,444,608 B2 | 5/2013 | Haslinger et al. |
| 8,721,624 B2 | 5/2014 | Wilson et al. |
| 9,216,274 B2 | 12/2015 | Arana et al. |
| 2001/0001812 A1 | 5/2001 | Valley et al. |
| 2001/0016702 A1 | 8/2001 | Benjamin |
| 2001/0029362 A1 | 10/2001 | Sirhhan et al. |
| 2001/0037085 A1 | 11/2001 | Keith et al. |
| 2002/0018866 A1 | 2/2002 | Lee et al. |
| 2002/0072755 A1 | 6/2002 | Bigus et al. |
| 2002/0082637 A1 | 6/2002 | Lumauig |
| 2002/0165523 A1 | 11/2002 | Chin et al. |
| 2003/0009151 A1 | 1/2003 | Wang |
| 2003/0032920 A1 | 2/2003 | Wantink |
| 2003/0055447 A1 | 3/2003 | Lee et al. |
| 2003/0105426 A1 | 6/2003 | Jorgensen |
| 2003/0125712 A1 | 7/2003 | Zhou |
| 2003/0139762 A1 | 7/2003 | Lee |
| 2004/0059291 A1 | 3/2004 | McDonnell et al. |
| 2004/0059292 A1 | 3/2004 | Hisamatsu et al. |
| 2004/0064130 A1* | 4/2004 | Carter ............... A61M 25/0045 604/523 |
| 2004/0068240 A1 | 4/2004 | Goodin et al. |
| 2004/0087901 A1 | 5/2004 | Rice et al. |
| 2004/0097892 A1 | 5/2004 | Evans et al. |
| 2004/0131808 A1 | 7/2004 | Schoenie et al. |
| 2004/0167441 A1 | 8/2004 | Reynolds et al. |
| 2004/0170782 A1 | 9/2004 | Wang et al. |
| 2004/0173935 A1 | 9/2004 | Lim et al. |
| 2004/0181206 A1 | 9/2004 | Chiu et al. |
| 2004/0191443 A1 | 9/2004 | Hamlin |
| 2004/0215141 A1 | 10/2004 | Clarke et al. |
| 2004/0267195 A1 | 12/2004 | Currlin |
| 2004/0267280 A1 | 12/2004 | Nishide et al. |
| 2005/0015048 A1 | 1/2005 | Chiu et al. |
| 2005/0043679 A1 | 2/2005 | Devens et al. |
| 2005/0124976 A1 | 6/2005 | Devens et al. |
| 2005/0131445 A1 | 6/2005 | Holman et al. |
| 2005/0148997 A1 | 7/2005 | Valley et al. |
| 2005/0154414 A1 | 7/2005 | Perreault et al. |
| 2005/0186370 A1 | 8/2005 | Hamilton et al. |
| 2005/0228429 A1 | 10/2005 | Burgmeier et al. |
| 2005/0238833 A1 | 10/2005 | Wang et al. |
| 2005/0277878 A1 | 12/2005 | Lee |
| 2006/0008606 A1 | 1/2006 | Horn et al. |
| 2006/0136032 A1 | 6/2006 | Legarda et al. |
| 2006/0165926 A1 | 7/2006 | Weber |
| 2006/0175739 A1 | 8/2006 | Hession et al. |
| 2006/0282041 A1 | 12/2006 | Melsheimer et al. |
| 2007/0060863 A1 | 3/2007 | Goeken et al. |
| 2007/0142771 A1 | 6/2007 | Durcan |
| 2007/0167973 A1 | 7/2007 | Stupecky et al. |
| 2007/0191813 A1 | 8/2007 | Chen |
| 2007/0240817 A1 | 10/2007 | Strong et al. |
| 2007/0260177 A1 | 11/2007 | Warnack |
| 2007/0276426 A1 | 11/2007 | Euteneuer |
| 2008/0015540 A1 | 1/2008 | Muni et al. |
| 2008/0045895 A1 | 2/2008 | Simpson et al. |
| 2008/0045928 A1 | 2/2008 | Simpson et al. |
| 2008/0065188 A1 | 3/2008 | Pallazza |
| 2008/0077085 A1 | 3/2008 | Eidenschink et al. |
| 2008/0221550 A1 | 9/2008 | Lee |
| 2008/0262470 A1 | 10/2008 | Lee et al. |
| 2009/0005754 A1 | 1/2009 | Soertermans |
| 2009/0156998 A1 | 6/2009 | Arana et al. |
| 2009/0247946 A1 | 10/2009 | Lee et al. |
| 2009/0264822 A1 | 10/2009 | Johnson |
| 2010/0010439 A1 | 1/2010 | Burgmeier et al. |
| 2010/0130925 A1 | 5/2010 | Haslinger et al. |
| 2011/0315301 A1 | 12/2011 | Simpson et al. |
| 2012/0065586 A1 | 3/2012 | Lee et al. |
| 2012/0143129 A1 | 6/2012 | Simpson et al. |
| 2012/0296273 A1 | 11/2012 | Arana et al. |
| 2013/0160932 A1 | 6/2013 | Simpson et al. |
| 2013/0178795 A1 | 7/2013 | Wilson et al. |
| 2013/0253425 A1 | 9/2013 | Haslinger et al. |
| 2014/0081310 A1 | 3/2014 | Lee et al. |

(56) References Cited

U.S. PATENT DOCUMENTS

| | | | |
|---|---|---|---|
| 2014/0163466 | A1 | 6/2014 | Arana et al. |
| 2014/0213967 | A1 | 7/2014 | Wilson et al. |
| 2015/0238737 | A1 | 8/2015 | Simpson et al. |

FOREIGN PATENT DOCUMENTS

| | | |
|---|---|---|
| EP | 0 420 488 | 3/1991 |
| EP | 0 737 487 | 10/1996 |
| EP | 0 821 979 | 2/1998 |
| EP | 0 904 795 | 3/1999 |
| EP | 0 931 558 | 7/1999 |
| EP | 0 962 227 | 12/1999 |
| EP | 1 103 280 | 5/2001 |
| EP | 1 287 846 | 3/2003 |
| JP | 10-290837 | 11/1998 |
| JP | 2001-018290 | 1/2001 |
| JP | 2001-353225 | 12/2001 |
| JP | 2005-167638 | 6/2005 |
| WO | WO 89/02763 | 4/1989 |
| WO | WO 93/20882 | 10/1993 |
| WO | WO 95/18647 | 7/1995 |
| WO | WO 96/03175 | 2/1996 |
| WO | WO 96/34646 | 11/1996 |
| WO | WO 97/26027 | 7/1997 |
| WO | WO 99/13924 | 3/1999 |
| WO | WO 01/34240 | 5/2001 |
| WO | WO 01/51115 | 7/2001 |
| WO | WO 01/89621 | 11/2001 |
| WO | WO 02/36194 | 5/2002 |
| WO | WO 02/36196 | 5/2002 |
| WO | WO 03/004248 | 1/2003 |
| WO | WO 2005/021083 | 3/2005 |
| WO | WO 2006/126311 | 11/2006 |
| WO | WO 2007/054364 | 5/2007 |
| WO | WO 2007/146572 | 12/2007 |
| WO | WO 2010/141765 | 12/2010 |

OTHER PUBLICATIONS

U.S. Appl. No. 12/477,695, Jan. 21, 2016 Final Office Action.
U.S. Appl. No. 13/562,810, Jan. 9, 2014 Issue Fee Payment.
U.S. Appl. No. 14/180,550, Nov. 17, 2015 Issue Fee Payment.
U.S. Appl. No. 14/230,581, Nov. 5, 2015 Issue Fee Payment.
U.S. Appl. No. 14/950,414, Feb. 8, 2016 Non-Final Office Action.
U.S. Appl. No. 14/230,581, Aug. 5, 2015 Notice of Allowance.
U.S. Appl. No. 12/477,695, Jan. 16, 2014 Final Office Action.
U.S. Appl. No. 12/477,695, Mar. 17, 2014 Response after Final Action.
U.S. Appl. No. 12/477,695, Apr. 10, 2014 Applicant Initiated Interview Summary.
U.S. Appl. No. 12/477,695, May 16, 2014 Amendment and Request for Continued Examination (RCE).
U.S. Appl. No. 12/477,695, Jul. 1, 2015 Non-Final Office Action.
U.S. Appl. No. 12/477,695, Oct. 1, 2015 Response to Non-Final Office Action.
U.S. Appl. No. 13/224,917, Dec. 10, 2014 Response to Non-Final Office Action.
U.S. Appl. No. 13/224,917, Mar. 2, 2015 Notice of Allowance.
U.S. Appl. No. 13/224,917, Mar. 25, 2015 Issue Fee Payment.
U.S. Appl. No. 13/775,699, Mar. 31, 2014 Issue Fee Payment.
U.S. Appl. No. 13/775,659, Jan. 26, 2015 Response to Non-Final Office Action.
U.S. Appl. No. 13/775,659, Feb. 17, 2015 Notice of Allowance.
U.S. Appl. No. 13/775,659, May 12, 2015 Issue Fee Payment.
U.S. Appl. No. 14/180,550, Apr. 13, 2015 Response to Non-Final Office Action.
U.S. Appl. No. 14/180,550, Aug. 17, 2015 Notice of Allowance.
U.S. Appl. No. 14/083,821, filed Nov. 19, 2013.
U.S. Appl. No. 12/324,425, Oct. 31, 2011 Amendment after Notice of Allowance.
U.S. Appl. No. 12/324,425, Sep. 22, 2011 Issue Fee payment.
U.S. Appl. No. 12/324,425, Aug. 31, 2011 Notice of Allowance.
U.S. Appl. No. 12/324,425, Jun. 6, 2011 Response to Non-Final Office Action.
U.S. Appl. No. 12/324,425, Mar. 4, 2011 Non-Final Office Action.
U.S. Appl. No. 11/480,143, Feb. 3, 2011 Issue Fee payment.
U.S. Appl. No. 11/480,143, Nov. 18, 2010 Notice of Allowance.
U.S. Appl. No. 11/480,143, Aug. 23, 2010 Response to Non-Final Office Action.
U.S. Appl. No. 11/480,143, Apr. 22, 2010 Non-Final Office Action.
U.S. Appl. No. 11/480,143, Feb. 18, 2010 Amendment and Request for Continued Examination (RCE).
U.S. Appl. No. 11/480,143, Feb. 4, 2010 Advisory Action.
U.S. Appl. No. 11/480,143, Jan. 15, 2010 Response to Final Office Action.
U.S. Appl. No. 11/480,143, Aug. 18, 2009 Final Office Action.
U.S. Appl. No. 11/480,143, May 27, 2009 Response to Non-Final Office Action.
U.S. Appl. No. 11/480,143, Jan. 27, 2009 Non-Final Office Action.
U.S. Appl. No. 11/480,143, Oct. 28, 2008 Response to Restriction Requirement.
U.S. Appl. No. 11/480,143, Oct. 17, 2008 Restriction Requirement.
U.S. Appl. No. 11/763,623, Jan. 29, 2013 Issue Fee payment.
U.S. Appl. No. 11/763,623, Oct. 29, 2012 Notice of Allowance.
U.S. Appl. No. 11/763,623, Oct. 17, 2012 Applicant Initiated Interview Summary.
U.S. Appl. No. 11/763,623, Oct. 21, 2010 Examiner Interview Summary.
U.S. Appl. No. 11/763,623, Aug. 24, 2010 Amendment and Request for Continued Examination (RCE).
U.S. Appl. No. 11/763,623, May 24, 2010 Notice of Appeal.
U.S. Appl. No. 11/763,623, Feb. 23, 2010 Final Office Action.
U.S. Appl. No. 11/763,623, Jan. 15, 2010 Response to Non-Final Office Action.
U.S. Appl. No. 11/763,623, Oct. 15, 2009 Non-Final Office Action.
U.S. Appl. No. 11/763,623, Jul. 20, 2009 Amendment and Request for Continued Examination (RCE).
U.S. Appl. No. 11/763,623, Mar. 20, 2009 Final Office Action.
U.S. Appl. No. 11/763,623, Mar. 3, 2009 Response to Non-Final Office Action.
U.S. Appl. No. 11/763,623, Dec. 3, 2008 Non-Final Office Action.
U.S. Appl. No. 11/763,623, Oct. 2, 2008 Response to Restriction Requirement.
U.S. Appl. No. 11/763,623, Sep. 25, 2008 Restriction Requirement.
U.S. Appl. No. 13/398,178, Jan. 25, 2013 Issue Fee payment.
U.S. Appl. No. 13/398,178, Oct. 25, 2012 Notice of Allowance.
U.S. Appl. No. 13/398,178, Oct. 16, 2012 Preliminary Amendment.
U.S. Appl. No. 11/958,106, May 21, 2013 Certificate of Correction.
U.S. Appl. No. 11/958,106, Feb. 20, 2013 Issue Fee payment.
U.S. Appl. No. 11/958,106, Nov. 20, 2013 Notice of Allowance.
U.S. Appl. No. 11/958,106, Oct. 23, 2012 Response to Non-Final Office Action.
U.S. Appl. No. 11/958,106, Aug. 1, 2012 Non-Final Office Action.
U.S. Appl. No. 11/958,106, May 29, 2012 Response to Notice of Non-Compliant.
U.S. Appl. No. 11/958,106, May 17, 2012 Notice of non-Compliant.
U.S. Appl. No. 11/958,106, May 7, 2012 Response to Non-Final Office Action.
U.S. Appl. No. 11/958,106, Jan. 6, 2012 Non-Final Office Action.
U.S. Appl. No. 11/958,106, Jun. 17, 2010 Amendment and Request for Continued Examination (RCE).
U.S. Appl. No. 11/958,106, Mar. 17, 2010 Final Office Action.
U.S. Appl. No. 11/958,106, Jan. 8, 2010 Response to Non-Final Office Action.
U.S. Appl. No. 11/958,106, Jul. 8, 2009 Non-Final Office Action.
U.S. Appl. No. 12/479,700, Sep. 22, 2011 Issue Fee payment.
U.S. Appl. No. 12/479,700, Aug. 22, 2011 Notice of Allowance.
U.S. Appl. No. 12/479,700, May 20, 2011 Response to Non-Final Office Action.
U.S. Appl. No. 12/479,700, May 13, 2011 Examiner Interview Summary.
U.S. Appl. No. 12/479,700, Apr. 27, 2011 Response to Non-Final Office Action.
U.S. Appl. No. 12/479,700, Oct. 24, 2010 Non-Final Office Action.

(56) References Cited

OTHER PUBLICATIONS

U.S. Appl. No. 12/479,700, Oct. 14, 2010 Response to Restriction Requirement.
U.S. Appl. No. 12/479,700, Oct. 4, 2010 Restriction Requirement.
U.S. Appl. No. 13/240,453, Nov. 19, 2013 Issue Fee payment.
U.S. Appl. No. 13/240,453, Aug. 20, 2013 Notice of Allowance.
U.S. Appl. No. 13/240,453, Apr. 30, 2013 Response to Non-Final Office Action.
U.S. Appl. No. 13/240,453, Apr. 17, 2013 Applicant Initiated Interview Summary.
U.S. Appl. No. 13/240,453, Dec. 5, 2012 Non-Final Office Action.
U.S. Appl. No. 13/240,453, Nov. 1, 2012 Response to Restriction Requirement.
U.S. Appl. No. 13/240,453, Oct. 2, 2012 Restriction Requirement.
U.S. Appl. No. 09/957,526, Jun. 6, 2006 Certificate of Correction.
U.S. Appl. No. 09/957,526, Jan. 24, 2005 Issue Fee payment.
U.S. Appl. No. 09/957,526, Nov. 4, 2004 Notice of Allowance.
U.S. Appl. No. 09/957,526, Sep. 21, 2004 Response to Non-Final Office Action.
U.S. Appl. No. 09/957,526, Jul. 1, 2004 Non-Final Office Action.
U.S. Appl. No. 09/957,526, Apr. 22, 2004 Amendment and Request for Continued Examination (RCE).
U.S. Appl. No. 09/957,526, Feb. 17, 2004 Final Office Action.
U.S. Appl. No. 09/957,526, Nov. 26, 2003 Response to Non-Final Office Action.
U.S. Appl. No. 09/957,526, Jun. 23, 2003 Non-Final Office Action.
U.S. Appl. No. 12/477,695, Sep. 20, 2013 Response to Non-Final Office Action.
U.S. Appl. No. 12/477,695, Jun. 20, 2013 Non-Final Office Action.
U.S. Appl. No. 12/477,695, Jan. 15, 2013 Amendment and Request for Continued Examination (RCE).
U.S. Appl. No. 12/477,695, Oct. 24, 2012 Advisory Action.
U.S. Appl. No. 12/477,695, Oct. 11, 2012 Response to Final Office Action.
U.S. Appl. No. 12/477,695, Aug. 15, 2012 Final Office Action.
U.S. Appl. No. 12/477,695, Apr. 16, 2012 Response to Non-Final Office Action.
U.S. Appl. No. 12/477,695, Dec. 16, 2011 Non-Final Office Action.
U.S. Appl. No. 10/392,697, Aug. 22, 2007 Issue Fee payment.
U.S. Appl. No. 10/392,697, May 31, 2007 Notice of Allowance.
U.S. Appl. No. 10/392,697, Feb. 26, 2007 Amendment and Request for Continued Examination (RCE).
U.S. Appl. No. 10/392,697, Jan. 5, 2007 Final Office Action.
U.S. Appl. No. 10/392,697, Sep. 29, 2006 Response to Non-Final Office Action.
U.S. Appl. No. 10/392,697, Jul. 13, 2006 Non-Final Office Action.
U.S. Appl. No. 10/392,697, May 1, 2006 Response to Restriction Requirement.
U.S. Appl. No. 10/392,697, Mar. 27, 2006 Restriction Requirement.
U.S. Appl. No. 13/224,917, Dec. 13, 2013 Response to Non-Final Office Action.
U.S. Appl. No. 13/224,917, Sep. 12, 2013 Non-Final Office Action.
U.S. Appl. No. 13/224,917, Aug. 23, 2013 Amendment and Request for Continued Examination (RCE).
U.S. Appl. No. 13/224,917, May 28, 2013 Final Office Action.
U.S. Appl. No. 13/224,917, Jan. 14, 2013 Response to Non-Final Office Action.
U.S. Appl. No. 13/224,917, Oct. 12, 2012 Non-Final Office Action.
U.S. Appl. No. 10/010,212, Mar. 6, 2006 Issue Fee payment.
U.S. Appl. No. 10/010,212, Feb. 9, 2006 Notice of Allowance.
U.S. Appl. No. 10/010,212, Dec. 27, 2005 Response to Final Office Action.
U.S. Appl. No. 10/010,212, Oct. 19, 2005 Final Office Action.
U.S. Appl. No. 10/010,212, Aug. 4, 2005 Response to Non-Final Office Action.
U.S. Appl. No. 10/010,212, May 6, 2005 Non-Final Office Action.
U.S. Appl. No. 10/010,212, Feb. 4, 2005 Amendment and Request for Continued Examination (RCE).
U.S. Appl. No. 10/010,212, Dec. 2, 2004 Final Office Action.
U.S. Appl. No. 10/010,212, Aug. 9, 2004 Response to Non-Final Office Action.
U.S. Appl. No. 10/010,212, Jun. 16, 2004 Non-Final Office Action.
U.S. Appl. No. 10/010,212, Mar. 22, 2004 Response to Non-Final Office Action.
U.S. Appl. No. 10/010,212, Dec. 31, 2003 Non-Final Office Action.
U.S. Appl. No. 10/010,212, Oct. 14, 2003 Amendment and Request for Continued Examination (RCE).
U.S. Appl. No. 10/010,212, Jul. 7, 2003 Final Office Action.
U.S. Appl. No. 10/010,212, Apr. 18, 2003 Response to Non-Final Office Action.
U.S. Appl. No. 10/010,212, Jan. 15, 2003 Non-Final Office Action.
U.S. Appl. No. 10/010,212, Dec. 17, 2002 Response to Restriction Requirement.
U.S. Appl. No. 10/010,212, Nov. 25, 2002 Restriction Requirement.
U.S. Appl. No. 12/687,265, Oct. 14, 2010 Issue Fee payment.
U.S. Appl. No. 12/687,265, Aug. 5, 2010 Notice of Allowance.
U.S. Appl. No. 13/562,810, Nov. 6, 2013 Notice of Allowance.
U.S. Appl. No. 13/562,810, Oct. 8, 2013 Response to Non-Final Office Action.
U.S. Appl. No. 13/562,810, Jul. 8, 2013 Non-Final Office Action.
U.S. Appl. No. 11/038,971, May 29, 2009 Issue Fee payment.
U.S. Appl. No. 11/038,971, Mar. 13, 2009 Notice of Allowance.
U.S. Appl. No. 11/038,971, Sep. 19, 2008 Response to Non-Final Office Action.
U.S. Appl. No. 11/038,971, Jul. 29, 2008 Non-Final Office Action.
U.S. Appl. No. 11/038,971, Feb. 28, 2008 Response to Non-Final Office Action.
U.S. Appl. No. 11/038,971, Nov. 28, 2007 Non-Final Office Action.
U.S. Appl. No. 11/038,971, Sep. 18, 2007 Response to Non-Final Office Action.
U.S. Appl. No. 11/038,971, Jun. 28, 2007 Non-Final Office Action.
U.S. Appl. No. 11/038,971, Apr. 12, 2007 Amendment and Request for Continued Examination (RCE).
U.S. Appl. No. 11/038,971, Feb. 16, 2007 Final Office Action.
U.S. Appl. No. 11/038,971, Nov. 13, 2006 Response to Non-Final Office Action.
U.S. Appl. No. 11/038,971, Sep. 21, 2006 Non-Final Office Action.
U.S. Appl. No. 11/196,134, Dec. 29, 2009 Issue Fee payment.
U.S. Appl. No. 11/196,134, Sep. 30, 2009 Notice of Allowance.
U.S. Appl. No. 11/196,134, Sep. 10, 2009 Amendment and Request for Continued Examination (RCE).
U.S. Appl. No. 11/196,134, Jun. 10, 2009 Final Office Action.
U.S. Appl. No. 11/196,134, Mar. 24, 2009 Response to Non-Final Office Action.
U.S. Appl. No. 11/196,134, Dec. 24, 2008 Non-Final Office Action.
U.S. Appl. No. 11/844,117, Aug. 2, 2011 Issue Fee payment.
U.S. Appl. No. 11/844,117, Jun. 15, 2011 Notice of Allowance.
U.S. Appl. No. 11/844,117, Mar. 23, 2011 Response to Non-Final Office Action.
U.S. Appl. No. 11/844,117, Nov. 23, 2010 Non-Final Office Action.
U.S. Appl. No. 11/844,117, Nov. 17, 2010 Amendment and Request for Continued Examination (RCE).
U.S. Appl. No. 11/844,117, Aug. 17, 2010 Final Office Action.
U.S. Appl. No. 11/844,117, Jun. 30, 2010 Response to Notice of Non-Compliant.
U.S. Appl. No. 11/844,117, Jun. 23, 2010 Notice of Non-Compliant.
U.S. Appl. No. 11/844,117, Jun. 17, 2010 Response to Non-Final Office Action.
U.S. Appl. No. 11/844,117, Mar. 17, 2010 Non-Final Office Action.
U.S. Appl. No. 11/844,117, Jan. 5, 2010 Response to Restriction Requirement.
U.S. Appl. No. 11/844,117, Oct. 13, 2009 Restriction Requirement.
U.S. Appl. No. 13/775,699, Dec. 31, 2013 Notice of Allowance.
U.S. Appl. No. 13/775,669, Oct. 28, 2013 Response to Restriction Requirement.
U.S. Appl. No. 13/775,699, Sep. 27, 2013 Restriction Requirement.
Cordis' Product Brochure; The Journey Inspires the Design, AQUA T3, Dec. 2002.

(56) References Cited

OTHER PUBLICATIONS

The Manufacturing Process Section of the Phelps Dodge High Performance Conductors Brochure, a Primer on Polymide Tubing, p. 1.
http://www.zeusinc.com/peek_resin.asp.
www.sigmaaldrich.com/img/assets/3900/Thermal_Transitions_of_Homopolymers.pdf.
Etherington & Roberts Dictionary, http://Palimpsest.stanford.edu/don/dt/dt1549.html.
Polymers: Structure and Properties, C.A. Daniels, Ph.D., P.E.; Technomic Publishing Co., Inc.
International Search Report for PCT/US2010/037313, dated Apr. 28, 2011.
International Search Report for PCT/US2007/071873, dated Apr. 14, 2008.
International Search Report for PCT/US2008/086270, dated Jun. 3, 2009.
U.S. Appl. No. 14/180,550, Jan. 13, 2015 Non-Final Office Action.
U.S. Appl. No. 13/224,917, Sep. 11, 2014 Non-Final Office Action.
U.S. Appl. No. 13/775,659, Oct. 24, 2014 Non-Final Office Action.

* cited by examiner

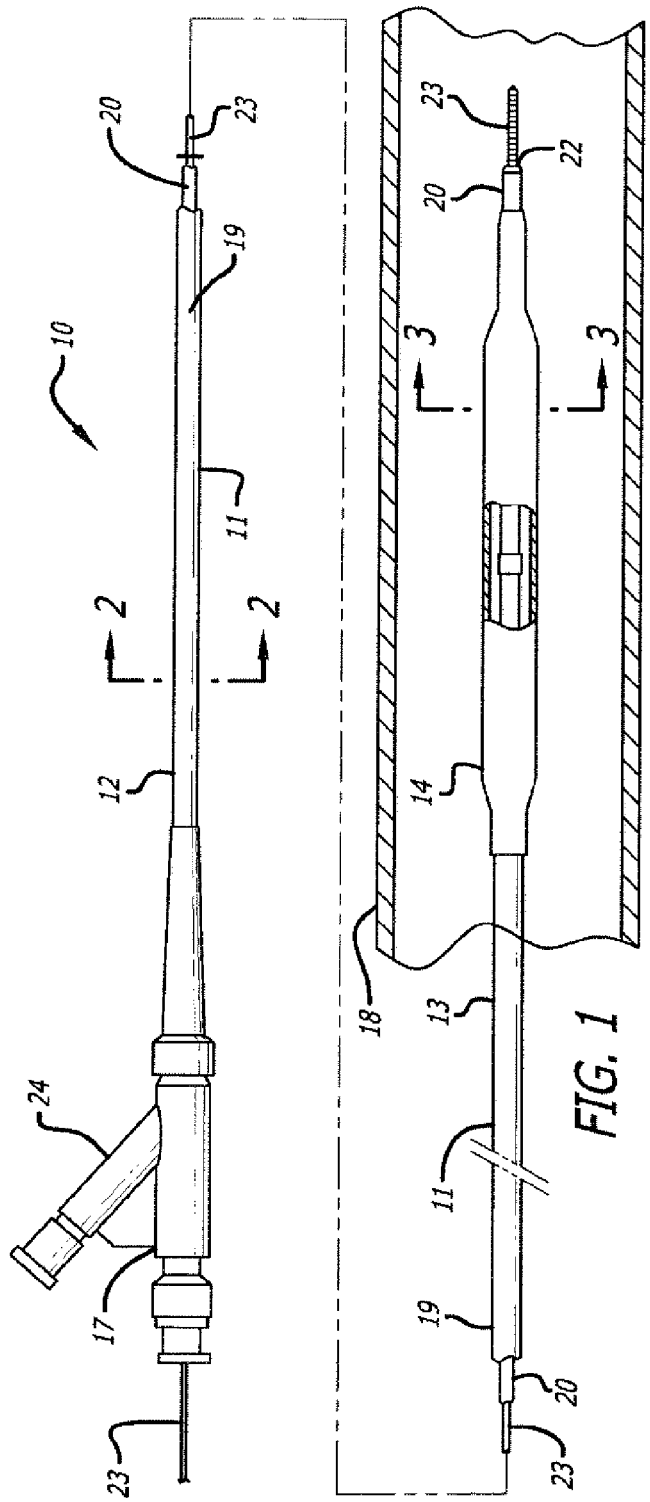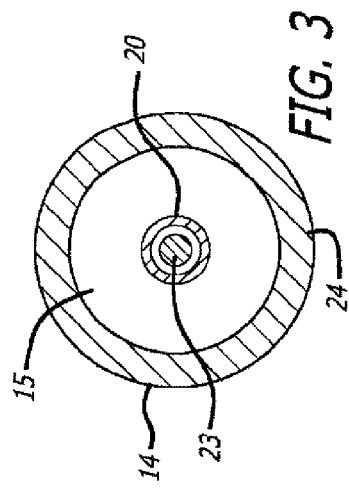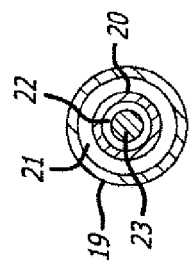

ROBUST CATHETER TUBING

CROSS-REFERENCES TO RELATED APPLICATIONS

This application is a continuation of U.S. patent application Ser. No. 12/478,929, filed Jun. 5, 2009, which is continuation-in-part of U.S. patent application Ser. No. 12/324,425 entitled "Low Compliant Catheter Tubing" filed Nov. 26, 2008, now U.S. Pat. No. 8,070,719, the contents each of which are incorporated by reference in their entirety.

BACKGROUND

The invention relates to the field of intravascular catheters, and more particularly to a balloon catheter or other catheter components, such as a guidewire enclosure and catheter tubing, that would benefit from the properties of the materials disclosed herein.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. The rate of expansion of the balloon for a given pressure is an important consideration in the design of the dilation catheter, as greater than anticipated expansion of the balloon against the vessel wall can cause trauma to the vessel wall. After the balloon is finally deflated, blood flow resumes through the dilated artery and the dilatation catheter can be removed from the patient's artery.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons and catheter tubing, material characteristics such as strength, flexibility and compliance must be tailored to provide optimal performance for a particular application. Angioplasty balloons and catheter tubing preferably have high strength for inflation at relatively high pressure, and high flexibility and softness for improved ability to track the tortuous anatomy. The balloon compliance, for example, is chosen so that the balloon will have a desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range. However, noncompliant balloons generally have relatively low flexibility and softness, making it more difficult to maneuver through various body lumens. Heretofore the art has lacked an optimum combination of strength, flexibility, and compliance, and particularly a low to non-compliant balloon with high flexibility and softness for enhanced trackability. Semi-compliant balloons made from semi-crystalline nylon 11, nylon 12, and copolymers of these nylons, such as poly ether block amide (for example, Pebax from Arkema) address these shortcomings and provide low distensibility and good flexibility, thus being used in many balloon dilatation catheters and stent delivery system.

For ease of thermal bonding to afore mentioned semi-compliant balloons, it is also preferred that the shaft of the balloon dilatation catheters and stent delivery system are also derived from same materials. Many balloon dilatation catheters and stent delivery systems therefore use shafts derived from these materials. The relative hardness and flexibility of the catheter tubing is also a constant compromise between the need for an agile tubing that can navigate the various body lumens, while having enough stiffness to be able to be pushed from a proximal end outside the body through the patient's vascular tract. A tubing that is relatively stiff will transmit proximal force more efficiently to the distal end, giving the practitioner more control over the location and position of the catheter balloon. However, stiffer tubing makes it much more difficult to bend or track curvatures in the body, leading to the paradox of the need for stiffer yet more flexible tubing. Moreover, stiffer materials when used to make catheter shafts have a higher tendency to kink, making it more difficult to control or push. Therefore, it is desirable to be able to increase stiffness and thus pushability by incorporating nylons having higher stiffness than semi-crystalline nylons having been used thus far. Some amorphous nylons offer desired higher stiffness than semi-crystalline nylons. However, the higher stiffness amorphous nylons are more susceptible to damage from solvents, such as isopropyl alcohol, used in the manufacturing, cleaning processes, and during clinical use. The present invention is directed to address this issue.

SUMMARY OF THE INVENTION

The softness and flexibility of a balloon or catheter tubing is a function of the flexural modulus of the polymeric material of the balloon, so that a balloon or tubing material having a higher Shore D durometer hardness, which yields a stronger and stiffer balloon or catheter tubing, has a higher flexural modulus. Conversely, a balloon or catheter tubing material having a lower Shore D durometer hardness, which thus provides a soft and flexible balloon or tubing, has a lower flexural modulus. The present invention is directed to a catheter tubing formed with a combination of at least two polyamides, a high durometer hardness material and a lower durometer hardness material.

The tubing can be made from a blend of the two polyamides, or a co-extrusion of the two polyamides with an inner layer and an outer layer. The first inner polyamide has a Shore D durometer hardness of greater than 78 D, more preferably Shore D durometer hardness of greater than 80 D, and can be preferably selected from various transparent amorphous nylons having segment such as an aliphatic segment, an aromatic segment, or a cycloaliphatic segment. The second outer polyamide has a lower durometer hardness than the first polyamide, and preferably less than 76 D, and preferably a block copolymer of nylon and polytetramethylene oxide (i.e. a copolyamide), or Pebax. The second outer polyamide is preferably semi-crystalline polyamide, thus providing enhanced resistance to solvents, such as isopropyl alcohol, used in the manufacturing, cleaning processes, and during clinical use. Both inner and outer polyamides preferably have the same amide block or segment, e.g. nylon 12, nylon 11, or nylon 6,6.

The preferred high hardness material is a nylon referred to as transparent amorphous nylon. The transparent amorphous nylon preferably has either an aliphatic segment, an aromatic segment, or a cycloaliphatic segment.

The catheter tubing of the invention may be formed by coextruding a tubular product formed from the two polymeric components to create a tubing having an outer layer and an inner layer of the two materials.

Various designs for balloon catheters well known in the art may be used in the catheter system of the invention. For example, conventional over-the-wire balloon catheters for angioplasty or stent delivery usually include a guidewire receiving lumen extending the length of the catheter shaft from a guidewire port in the proximal end of the shaft. Rapid exchange balloon catheters for similar procedures generally include a short guidewire lumen extending to the distal end of the shaft from a guidewire port located distal to the proximal end of the shaft.

In the case of a robust co-extruded catheter shaft, an inner layer can be comprised of a high modulus or high Shore D durometer nylon, preferably a Shore D durometer value greater than 80, such as Grilamid TR55 LX nylon 12 from EMS—American Grilon Inc., which provides a high modulus for enhanced pushability. Also, it would be beneficial if the glass transition temperature of the high modulus polymer forming the inner layer is greater than 100° C., and more preferably greater than 120° C. However, the TR55 LX or other high modulus amorphous nylon has a greater tendency to kink and is susceptible to attack by solvents. To combat the kink propensity and to protect the catheter shaft from solvents, a thin outer layer of lower modulus material such as Pebax is formed over the TR55 LX inner layer to serve as a protective layer and to resist kinking of the shaft. The outer layer can be selected from semi-crystalline polyamide or more preferably from a copolyamide of lower durometer value such as Pebax 72 D, Pebax 63 D, and the like, where the Shore D durometer value is less than 76.

By incorporating an amorphous polyamide such as TR 55 LX as one layer, the dimensional stability is increased for as the shelf life of the catheter increases due to the higher glass transition temperature, as compared with nylon 12 or Pebax which has a glass transition temperature at or below 55° C. Also, a higher tensile strength (approximately 11,000 psi) of amorphous nylon TR 55 LX compared with nylon 12 or Pebax (7,500-8,200) provides a higher rupture limit with the same wall thickness.

The co-axial tubing can be formed into a tapered configuration, where the radius of the shaft gradually reduces until the balloon attachment point. This gradual reduction in the radial component of the shaft serves to eliminate the mid-shaft portion of the catheter, which simplifies the manufacturing process by avoiding a laser operation or other mechanism to attach the mid-shaft.

BRIEF DESCRIPTION OF THE DRAWINGS

FIG. 1 is an elevated view partially in section of a balloon catheter which embodies features of the invention, showing the balloon in an expanded state;

FIG. 2 is a transverse cross sectional view of the balloon catheter of FIG. 1 taken along lines 2-2;

FIG. 3 is a transverse cross sectional view of the balloon catheter of FIG. 1 taken along lines 3-3.

DETAILED DESCRIPTION OF THE PREFERRED EMBODIMENTS

Figure 4:
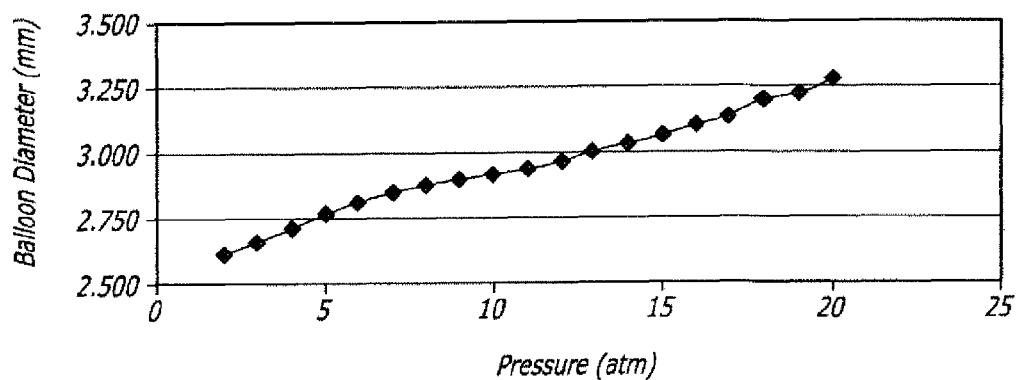
FIG. 4 is a graph of the compliance of the catheter balloon using a first preferred blend of materials.

In angioplasty balloons, an object is to apply a high pressure to the interior wall of the lumen to compress the plaque and/or to fully expand the stent. This relies on a robust balloon with a sturdy out wall and a high pressure capability. The compliance of the balloon, i.e., the expansion of the balloon as a function of internal pressure, is preferably low or flat to more accurately control the amount of pressure applied to the arterial wall. However, the deliverability of the balloon is also a factor, especially where tortuous body lumens are involved. Stiff balloons (i.e., high modulus materials) tend to have poor flexibility and lack the maneuverability to navigate the various body lumens, and thus make poor choices for catheter balloons. Conversely, flexible balloons (low modulus materials) that have high compliance are poorly suited to apply a precise known pressure on the arterial wall due to a high expansion rate per applied pressure. The goal is thus to increase the rupture strength by adding the high modulus material such as nylon to the softer polyamide material.

Soft polyamide materials such as Pebax® are semi-crystalline polymers and usually include an amorphous segment. The amorphous segment has a lower density than the crystalline structure and thus is weaker in general than crystalline segments. If the amorphous segment can be reinforced by adding a small amount of a higher modulus material the response of the amorphous segment can be delayed and the overall strength of the material can be strengthened. The high modulus material preferably has a Shore D durometer hardness of 78 D or more. Suitable materials include transparent amorphous nylon such as nylon 12, and more preferably a nylon 12 with a aliphatic segment, an aromatic segment, or a cycloaliphatic segment. These nylons are transparent amorphous because they are essentially amorphous, lacking the crystalline structure of other more conventional nylon 12. The aliphatic segment, aromatic segment, or cycloaliphatic segment does not crystallize with the main chain, disrupting the formation of longer crystalline chains in the polymer. The amorphous segment of the transparent amorphous nylon 12 combines with the amorphous segment of the Pebax to strengthen the Pebax by enhancing the weakest link in the chain, thereby increasing the overall strength of the polymer.

FIG. 1 illustrates a balloon catheter which embodies features of the invention. The catheter 10 of the invention generally comprises an elongated catheter shaft 11 having a proximal section, 12 a distal section 13, an inflatable balloon 14 formed of a blend of polymeric materials on the distal section 13 of the catheter shaft 11, and an adapter 17 mounted on the proximal section 12 of shaft 11. In FIG. 1, the catheter 10 is illustrated within a patient's body lumen 18, prior to expansion of the balloon 14.

In the embodiment illustrated in FIG. 1, the catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

FIGS. 2 and 3 show transverse cross sections of the catheter shaft 11 and balloon 14, respectively, illustrating the guidewire receiving lumen 22 of the guidewire's inner tubular member 20 and inflation lumen 21 leading to the balloon interior 15. The balloon 14 can be inflated by radiopaque fluid introduced at the port in the side arm 24 into inflation lumen 21 contained in the catheter shaft 11, or by other means, such as from a passageway formed between the outside of the catheter shaft and the member forming the balloon, depending on the particular design of the catheter. The details and mechanics of balloon inflation vary according to the specific design of the catheter, and are well known in the art.

Non-compliant or low-compliant balloon 14 and/or the shaft 11 is formed of a blend of a first polyamide having a Shore D durometer hardness greater than 78 D and a copolyamide of lower durometer hardness, preferably less than 76 D. A preferred polyamide having a Shore D durometer hardness greater than 78 D is an amorphous polyamide such as EMS TR 55 (transparent amorphous nylon 12), Arkema Rilsan G110 (transparent amorphous nylon 12), or Cristamid MS 110 (transparent amorphous nylon 12). The polyamide is preferably includes a cycloaliphatic segment, an aromatic segment, or an aliphatic segment. Such polyamides are also referred to as transparent polyamide. The preferred copolyamide material for forming the polymeric blend for the balloon is Pebax, and more preferably Pebax 72 D, Pebax 70 D, Pebax 63 D, or Pebax 55 D. Alternatively, the copolyamide of lower durometer hardness is preferably a block copolymer of nylon 12 and polytetramethylene oxide.

The flexural modulus of the polyamide is preferably greater than 1700 MPa (240,000 psi) and the flexural modulus of the copolyamide is less than 850 MPa (120,000 psi). The tensile strength at break of both polyamides is at least 50 MPa, and elongation at break of both polyamides is at least 150%.

The catheter shaft will generally have the dimensions of conventional dilatation or stent deploying catheters. The length of the catheter 10 may be about 90 cm to about 150 cm, and is typically about 135 cm. The outer tubular member 19 has a length of about 25 cm to about 40 cm, an outer diameter (OD) of about 0.039 in to about 0.042 in, and an inner diameter (ID) of about 0.032 in. The inner tubular member 20 has a length of about 25 cm to about 40 cm, an OD of about 0.024 in and an ID of about 0.018 in. The inner and outer tubular members may taper in the distal section to a smaller OD or ID.

The length of the compliant balloon 14 may be about 1 cm to about 4 cm, preferably about 0.8 cm to about 4.0 cm, and is typically about 2.0 cm. In an expanded state, at nominal pressure of about 8 to about 10 atm, the balloon diameter is generally about 0.06 in (1.5 mm) to about 0.20 in (5.0 mm). and the wall thickness is about 0.0006 in (0.015 mm) to about 0.001 in (0.025 mm), or a dual wall thickness of about 0.025 mm to about 0.056 mm. The burst pressure is typically about 20 to 26 atm, and the rated burst pressure is typically about 18 atm.

In a presently preferred embodiment, the balloon 14 may include wings, which may be folded into a low profile configuration (not shown) for introduction into and advancement within the patient's vasculature. When inflating the balloon to dilate a stenosis, the catheter 10 is inserted into a patient's vasculature to the desired location, and inflation fluid is delivered through the inflation lumen 21 to the balloon 14 through the inflation port 24. The semi-compliant or noncompliant balloon 14 expands in a controlled fashion with limited radial expansion, to increase the size of the passageway through the stenosed region. Similarly, the balloon has low axial growth during inflation, to a rated burst pressure of about 14 atm, of about 5 to about 10%. The balloon is then deflated to allow the catheter to be withdrawn. The balloon may be used to deliver a stent (not shown), which may be any of a variety of stent materials and forms designed to be implanted by an expanding member, see for example U.S. Pat. No. 5,514,154 (Lau et al.) and U.S. Pat. No. 5,443,500 (Sigwart), incorporated herein in their entireties by reference.

EXAMPLE 1

A proximal shaft for the over-the-wire catheter may have a tapered tubing coextruded and tapered with TR55 inner layer and Pebax 72 D outer layer. The proximal wall thickness of TR55 may be approximately 0.005" and a proximal wall thickness of Pebax 72 D may be approximately 0.001". A distal wall thickness of TR55 is approximately 0.002" and a distal wall thickness of Pebax 72 D is approximately 0.001". In addition to balloons, the blended composition has usefulness as other parts of the catheter, such as the guidewire enclosure 20 of FIGS. 1-3. The inner member of the multi-layered tubing can have a lubricious inner layer (HDPE. UHMWPE, and the like) with bonding mid layer and polymer blend outer layer. Like the catheter balloon, the blend is comprised of one polymer having a Shore D durometer greater than 78 and another polymer having lower durometer, preferably less than 76 D. Both polyamides preferably have same amide block or segment, i.e. one type of amide (nylon) block, solely comprised of nylon 12, nylon 11, nylon 6, or nylon 6, 6 but not combination of these.

The polyamide having Shore D durometer greater than 78 D is preferably amorphous polyamide selected from polyamide such as EMS TR 55 (transparent amorphous nylon 12), Arkema Rilsan G110 (transparent amorphous nylon 12), or Cristamid MS 110 (transparent amorphous nylon 12). This polyamide is preferably a copolyamide comprising cycloaliphatic, and/or aromatic, and/or aliphatic segment. The other copolyamide of lower durometer is preferably a block copolymer of nylon 12 and polytetramethylene oxide, such as Pebax 72 D, Pebax 70 D or Pebax 63 D.

The high durometer polymer serves to increase resistance to collapse of the tubing and provides enhanced pushability while the lower durometer polymer provides flexibility and kink resistance. Although it is preferred to have blends of high miscibility, the blend ratio is such that the lower durometer polymer forms a "virtual" continuous phase while the higher durometer polymer forms "virtual" reinforcement.

Figure 5:
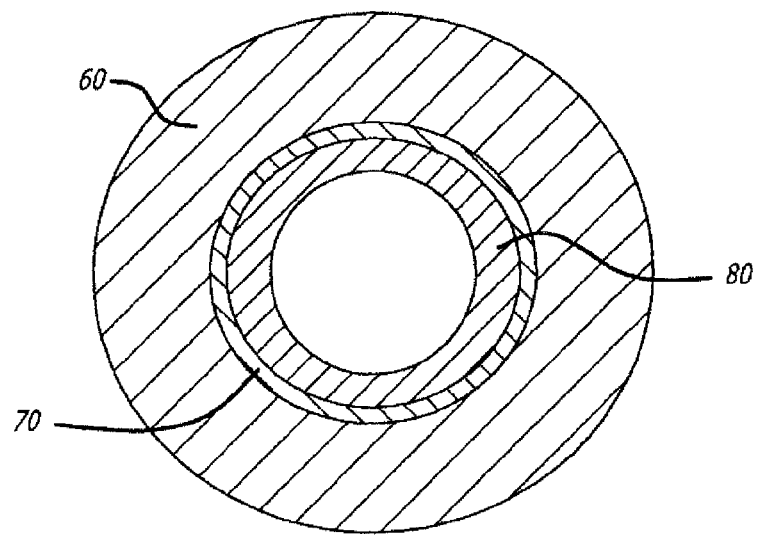
FIG. 5 is a cross-sectional view of a catheter shaft with an inner layer, an intermediate layer, and an outer layer.

As shown in FIG. 5, an outer layer 60 of the catheter shaft can be comprised of an amorphous polyamide selected from polyamide such as EMS TR 55 (transparent amorphous nylon 12), Arkema Rilsan G110 (transparent amorphous nylon 12), Cristamid MS 110 (transparent amorphous nylon 12), polyamide 11, polyamide 6, or polyamide 6,6. This polyamide is preferably a copolyamide comprising cycloaliphatic, and/or aromatic, and/or aliphatic segment. In one embodiment, the outer layer 60 is blended with a softer polyamide such as a crystalline or semi-crystalline copolymer of nylon 12 and polytetramethylene oxide or polytetramethylene glycol, e.g. Pebax 72 D or Pebax 70 D. This blending offers a higher strength outer layer that offers higher pushability and resists collapse, while the copolymer operates to resist kinking and yield greater flexibility. Although it is preferable to have blends of high miscibility, blend ratios are such that the lower durometer polymer forms a virtual continuous phase and the high durometer polymer forms a virtual reinforcement. The intermediate layer 70 is a bonding layer, such as Primacore, to meld the inner and outer layers together. The inner layer 80 can be a lubricious material that reduces the friction of a guide wire passing through the lumen 90, such as HDPE or UHM-WPE. Other materials are also contemplated, as long as the outer layer has a glass transition or melting temperature that is preferably lower than, or at least approximately equal to, the surface temperature of the mold during the blowing or forming process of the balloon.

Figure 6:
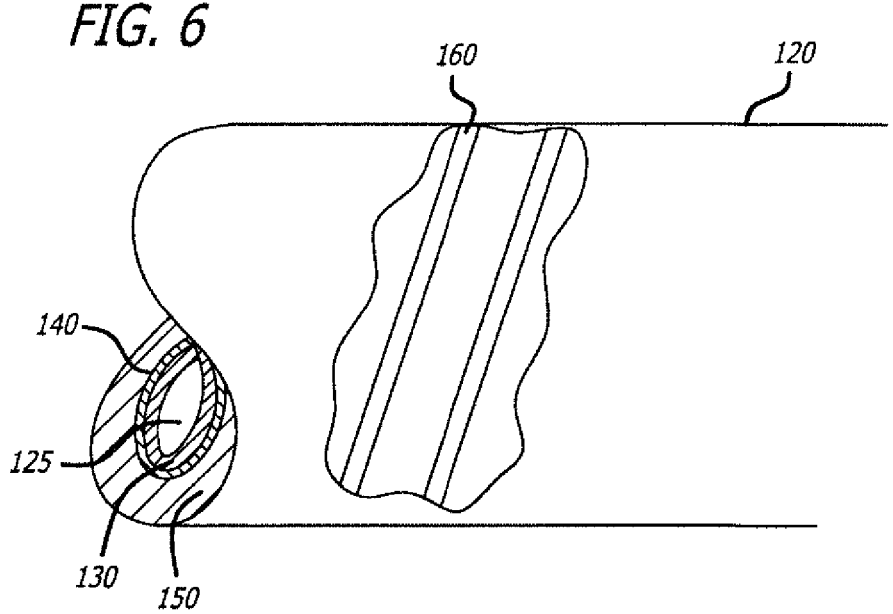
FIG. 6 is an enlarged, partially cut-away view of a catheter shaft illustrating multiple layers, including an embedded high strength ribbon or coil in the outer layer.

FIG. 6 shows another embodiment of a catheter shaft 120 having a lumen 125 extending therein, the shaft 120 having an inner layer 130 comprising a low friction material such as high density polyethylene and an intermediate layer 140 serving as a bonding layer. An outer layer comprising a first polymer having a first Shore D durometer value of no greater than 76 D, such as Pebax 72 D or Pebax 63 D is impregnated with a second polymer having a Shore D durometer value that is greater than the first Shore D durometer value, and preferably greater than 78 such as TR55 or the other transparent nylon 12 materials discussed above. The second polymer 160 can be wrapped around the shaft 120 like a helix or coil to reinforce the outer layer 150.

Figure 7:
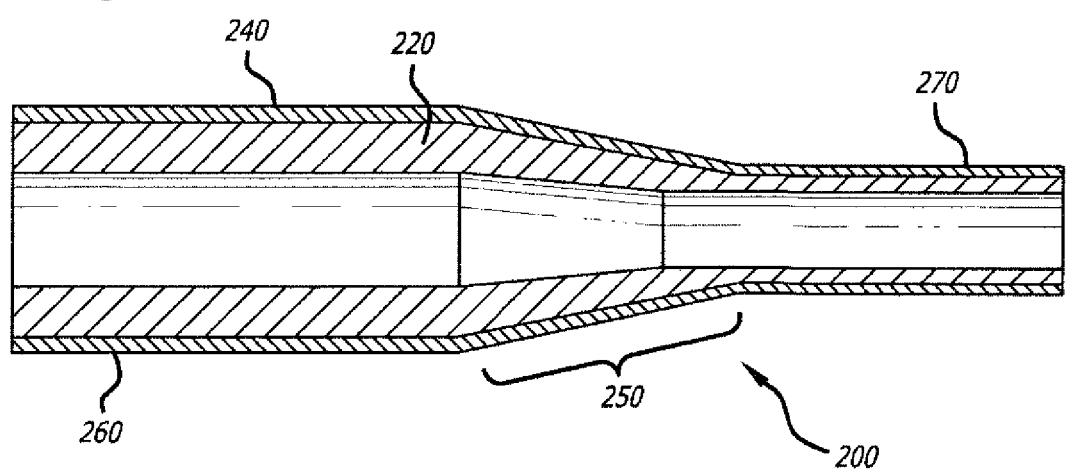
FIG. 7 is an enlarged, cross-sectional view of another embodiment of a catheter shaft.

FIG. 7 illustrates another embodiment of a catheter shaft having an inner layer 220 of a high modulus material with a high Shore D durometer value such as amorphous nylon 12. This inner layer material provides a high strength catheter shaft for higher pushability. However, the transparent nylon 12 has a tendency to kink, and it is susceptible to solvents used in cleaning or other manufacturing processes. To resist kinking, and to protect the catheter from solvents, a thin outer layer 240 of Pebax or other soft copolyamide is formed over the inner layer 220. The two layers 220, 240 can be co-extruded in a single operation to create the shaft 200 of FIG. 7. The shaft 220 also incorporates a tapered section 250 as the shaft transitions from a main body portion to the portion 260 to the portion 270 where a balloon may be attached. In existing catheter shafts, this section requires a mid shaft section that must be separately attached to the catheter shaft using expensive laser equipment. The tapered transition from the main body portion 260 to the balloon attachment portion 270 eliminates the need for a mid shaft and thus the need for the laser equipment and assembly line personnel required to operate the laser equipment, resulting in a more efficient and cost effective catheter.

The shaft of FIG. 7 preferably has both co-extruded layers 220, 240 with a common amide block or segment for better adhesion or compatibility, i.e., one type of amide (nylon) block, comprising one and only one of nylon 12, nylon 11, nylon 6, or nylon 6,6. The inner polymer is preferably a polyamide having a Shore D durometer value of greater than 78, such as amorphous polyamide selected from EMS TR55, Arkema Rilsan G110, or Cristamid MS 110, all commonly referred to as transparent nylon 12. This polyamide preferably comprises cycloaliphatic, aromatic, and/or aliphatic segments. The outer layer 240 may preferably be a copolyamide block copolymer of nylon 12 and polytetramethylene glycol.

Various embodiments are described above in effort to illustrate the concepts of the present invention, but these embodiments are not intended to be limiting or exclusive. Rather, the scope of the invention is to be determined by the words of the appended claims, interpreted in the context of the above description but not limited to those examples and embodiments described above and shown in the Figures.

We claim:

1. A method of forming an elongated, flexible catheter, comprising:
    forming a shaft having a proximal end, a distal end, and a lumen extending therein, the shaft having an inner layer comprising an amorphous polyamide having a Shore D durometer value of greater than 78, and an outer layer comprising a semi-crystalline polyamide or copolyamide having a Shore D durometer value of less than 76, wherein the outer layer is thinner than the inner layer, the shaft having an increased resistance to kinking as compared to a similar shaft of a single layer of the amorphous polyamide having a Shore D durometer value of greater than 78; and
    providing a working device disposed on the distal end of the shaft.

2. The method of claim 1, wherein the working device is an inflatable balloon.

3. The method of claim 1, wherein the amorphous polyamide of the inner layer has a glass transition temperature of greater than 100° C.

4. The method of claim 1, wherein the polyamide or copolyamide of the outer layer has a glass transition temperature of less than 55° C.

5. The method of claim 1, wherein the amorphous polyamide of the inner layer and the polyamide or copolyamide of the outer layer have a common amide block.

6. The method of claim 5, wherein the common amide block is selected from the group consisting of nylon 12, nylon 11, nylon 6, and nylon 6,6.

7. The method of claim 1, wherein the inner polyamide includes at least one segment selected from the group consisting of cycloaliphatic segments, aliphatic segments, and aromatic segments.

8. The method of claim 1, wherein the inner polyamide comprises at least two segments selected from the group consisting of aliphatic segments, aromatic segments, and cycloaliphatic segments.

9. The method of claim 1, wherein the inner and outer layers are fowled by co-extrusion.

10. The method of claim 9, wherein the catheter shaft is tapered.

11. The method of claim 9, wherein the catheter shaft has a necked diameter portion.

12. The method of claim 1, wherein the outer layer is a polymer of nylon or a block copolymer of nylon.

13. The method of claim 12, wherein the nylon is nylon 11, nylon 12, nylon 6, nylon 6,6 or nylon 6,12.

14. The method of claim 12, wherein the block copolymer is a block copolymer of nylon and polytetramethylene oxide.

15. The method of claim 14, wherein the nylon is nylon 11, nylon 12, nylon 6, nylon 6,6 or nylon 6,12.

16. The method of claim 1, wherein the outer layer comprises a block copolymer of nylon 12 and polytetramethylene oxide.

17. The method of claim 1, wherein the shaft has an enhanced resistance to solvents as compared to a similar shaft of a single layer of the amorphous polyamide having a Shore D durometer value of greater than 78.

18. The method of claim 1, wherein the outer layer is thinner than the inner layer along substantially an entire length of the shaft extending from the proximal end to the distal end.

19. A method of forming an elongated, flexible catheter, comprising:
   forming a shaft having a proximal end, a distal end, and a lumen extending therein, the shaft having an inner layer comprising high density polyethylene and an outer comprising a blend of two polymers, including a first polymer being an amorphous nylon having a Shore D durometer value of greater than 78 and a second polymer having a Shore D durometer value of no more than 76, wherein the inner layer is thicker than the outer layer, the shaft having an increased resistance to kinking as compared to a similar shaft having an inner layer of the high density polyethylene and an outer layer of the amorphous nylon having a Shore D durometer value of greater than 78; and
   providing a working device disposed on the distal end of the shaft.

20. The method of claim 19, further comprising forming an intermediate layer disposed between the inner layer and the outer layer, the intermediate layer serving as a bonding layer.

21. The method of claim 19, wherein the first polymer and the second polymer have a common amide block.

22. The method of claim 21, wherein the common amide block is selected from the group consisting of nylon 12, nylon 11, nylon 6, and nylon 6,6.

23. The method of claim 19, wherein the first polymer includes at least one segment selected from the group consisting of cycloaliphatic segments, aliphatic segments, and aromatic segments.

24. The method of claim 19, wherein the first polymer comprises at least two segments selected from the group consisting of aliphatic segments, aromatic segments, and cycloaliphatic segments.

25. The method of claim 19, wherein the inner layer and outer layer are formed by co-extrusion.

26. The method of claim 19, wherein the second polymer is a semi-crystalline polymer of nylon or a block copolymer of nylon.

27. The method of claim 26 wherein the nylon is nylon 11, nylon 12, nylon 6, nylon 6,6 or nylon 6,12.

28. The method of claim 19, wherein the block copolymer is a block copolymer of nylon and polytetramethylene oxide.

29. The method of claim 19, wherein the shaft has an enhanced resistance to solvents as compared to a similar shaft having an inner layer of the high density polyethylene and an outer layer of the amorphous nylon having a Shore D durometer value of greater than 78.

30. The method of claim 19, wherein the outer layer is thinner than the inner layer along substantially an entire length of the shaft extending from the proximal end to the distal end.

\* \* \* \* \*